United States Patent [19]

Thorogood

[11] 4,317,830

[45] Mar. 2, 1982

[54] TREATMENT OF SHOCK

[75] Inventor: Peter B. Thorogood, London, England

[73] Assignee: Burroughs Wellcome Co., Research Triangle Park, N.C.

[21] Appl. No.: 67,397

[22] Filed: Aug. 17, 1979

Related U.S. Application Data

[63] Continuation-in-part of Ser. No. 952,796, Oct. 19, 1978, abandoned, which is a continuation-in-part of Ser. No. 936,407, Aug. 24, 1978, abandoned.

[30] Foreign Application Priority Data

Aug. 26, 1977 [GB] United Kingdom ............... 35912/77
Feb. 1, 1978 [GB] United Kingdom ................. 3983/78
Aug. 8, 1978 [GB] United Kingdom ............... 32536/78

[51] Int. Cl.$^3$ .......................................... A61K 31/415
[52] U.S. Cl. ............................................... 424/273 R
[58] Field of Search ..................................... 424/273 R

[56] References Cited

U.S. PATENT DOCUMENTS 3,300,511  1/1967  Zeile et al. ........................... 424/273
3,711,487  1/1973  Draber et al. ........................ 424/273

FOREIGN PATENT DOCUMENTS 3211  10/1978  European Pat. Off. ............ 424/273
2533211  10/1977  Fed. Rep. of Germany ...... 424/273
1364312  8/1974  United Kingdom ................ 424/273

OTHER PUBLICATIONS

Moncada et al., "Prostaglandins", 13(4) pp. 611-618.
"Biochemical Pharmacology", 23, 2377-2386; 24, 1902-1903.
Tai & Yuan, "Biochem. & Biophys. Res. Comm.", 80(1), 236-242.
"J. Clin. Invest.", vol. 65, Jan. 1980, 227-230, European specification, 3211.

*Primary Examiner*—Frederick E. Waddell
*Attorney, Agent, or Firm*—Donald Brown

[57] ABSTRACT

The invention relates to a class of imidazoles substituted by cycloalkyl or cycloalkenyl which have pharmacological properties making them useful in medicine, in particular in the prophylaxis and treatment of thromboembolic disorders, and also of shock and angina pectoris.

11 Claims, No Drawings

TREATMENT OF SHOCK

CROSS REFERENCE TO EARLIER APPLICATIONS

This application is a continuation-in-part of my application Ser. No. 952,796 filed Oct. 19, 1978, now abandoned, which is in turn a continuation-in-part of my application Ser. No. 936,407 filed Aug. 24, 1978, now abandoned.

The present invention relates to imidazole derivatives and salts thereof, to their synthesis and intermediates therefor, to pharmaceutical formulations containing such compounds and to the use of these compounds in medicine.

Thromboxane $A_2$ ($TXA_2$), a potent stimulator of blood platelet aggregation, is produced, in platelets, from the prostaglandin endoperoxides $PGG_2$ and $PGH_2$. Prostacyclin ($PGI_2$), which has potent anti-aggregatory activity, is also produced (in blood vessel walls) from $PGG_2$ and $PGH_2$ and it has been suggested that a balance between the production of $TXA_2$ and $PGI_2$ is the controlling factor in thrombus formation. It would, in consequence, be desirable in the treatment and prophylaxis of thrombo-embolic disorders to be able to selectively inhibit $TXA_2$ synthetase, thereby favouring the production of the anti-aggregatory agent $PGI_2$.

Imidazole and 1-methylimidazole are known to provide some degree of inhibition of the enzymic conversion of the endoperoxides ($PGG_2$ and $PGH_2$) to thromboxane $A_2$ by platelet microsomes (Moncada et al., Prostaglandins, 13/4, 611–618, 1977). Certain 1-n-alkylimidazoles, especially 1-n-dodecylimidazole and its higher homologues have been described as being capable of lowering serum cholesterol levels (U.K. Pat. No. 1,364,312; Biochem. Pharmacol. 24, 1902–1903, 1975).

We have now discovered that $TXA_2$ synthetase may be inhibited by 1-alkylimidazoles of formula (I) and acid addition salts thereof. The compounds of formula (I) and their salts are hereinafter referred to as the "active compounds".

The compounds of formula (I) are novel and of formula:

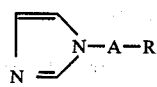
(I)

in which A is a straight or branched, saturated or unsaturated acyclic hydrocarbon radical of from 1 to 3 carbon atoms, i.e. 1, 2 or 3 carbon atoms, and R is a cycloalkyl or cycloalkenyl radical of from 4 to 9, preferably from 5 to 8, especially 7 or 8, carbon atoms and optionally substituted by one, two, three or more alkyl radicals each containing from 1 to 4 carbon atoms with the proviso that when A is a methylene radical R is not unsubstituted cyclohexyl.

In formula (I) examples of cycloalkyl radicals are cyclobutyl, cyclopentyl, cyclohexyl, cycloheptyl, and cyclooctyl; cycloalkenyl radicals include cyclohex-3-enyl, cyclopentenyl, 1,4-cyclohexadienyl and cyclohept-2-enyl.

A valuable class of compounds of formula (I) are those in which R is cyclohexyl, cycloheptyl, cyclooctyl or cycloalkenyl of 6 to 8 carbon atoms and A is —$CH_2$— or —$(CH_2)_2$—. Compounds of formula (I) may also be used as acid addition salts thereof, especially as pharmaceutically acceptable ones.

Especially preferred compounds include:
1-Cyclooctylmethylimidazole,
1-Cyclohex-3-enylmethylimidazole,
1-(2-Cyclohexylethyl)imidazole,
1-Cycloheptylmethylimidazole
and acid addition salts thereof.

Other potent compounds include:
1-Cyclopentylmethylimidazole,
1-(4-Methylcyclohexylmethyl)imidazole,
1-Cyclobutylmethylimidazole,
1-Cyclooctylvinylimidazole,
1-(1-Cyclooctylethyl)imidazole,
1-(2-Cyclooctylethyl)imidazole,
1-(3-Cyclooctylpropyl)imidazole,
1-(Cyclohept-2-enylmethyl)imidazole,
1-Cyclononylmethylimidazole,
1-[2-(cyclohex-3-enyl)ethyl]imidazole
and acid addition salts thereof.

In contrast to imidazole and 1-methylimidazole the compounds of formula (I) are more potent inhibitors of $TXA_2$ synthetase. Many of the compounds (for example in (I) R is cycloalkyl or cycloalkenyl, and A is —$CH_2$— or —$(CH_2)_2$— are also more selective in their action in not inhibiting other anti-aggregatory-prostaglandin generating enzymes such as cyclo-oxygenase. The compounds of formula (I) also do not produce the side effects found with imidazole upon in vivo administration. The compounds of formula (I) are further capable of inhibiting platelet aggregation in vivo and also are capable of disaggregating platelet clumps. The compounds 1-cyclooctylmethylimidazole, 1-cyclohex-3-enylmethylimidazole, 1-(2-cyclohexylethyl)imidazole, 1-cycloheptylmethylimidazole and their salts especially display these properties.

The compounds of formula (I) are suitable for use in the treatment or prophylaxis of angina pectoris. In some cases it is possible to prevent the onset of angina pectoris, for example when a patient with coronary artery disease is given cardiac pacing, which leads generally to an increase of $TXA_2$ in the blood, and which is associated with the onset of angina pectoris. Also, inhibition of $TXA_2$ formation prevents or delays the onset of shock, e.g. experimentally induced shock in laboratory animals.

Imidazoles of formula (I) and acid addition salts thereof may be made by any method known in the art for the synthesis of compounds of analogous structure. In general these methods comprise linking the imidazole ring to the remainder of the molecule; converting a precursor molecule by elimination of a functional group from the imidazole ring; and formation of the desired compound from a corresponding imidazoline, pyrazole or unsaturated analogue.

A most convenient method of synthesis involves the reaction of imidazole (formula (II)) or a salt thereof with an alkylating agent of formula (III):

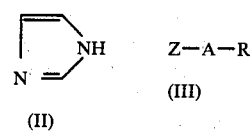
(II)   (III)

wherein R and A are as defined in formula (I) and Z is a leaving group. This reaction is well established in the literature, and the leaving group may be chosen from a variety of substituents but especially halo, preferably chloro or bromo, or from p-toluenesulphonyloxy but other arylsulphonyloxy, alkanesulphonyloxy or aralkylsulphonyloxy radicals may be used. The reaction is preferably performed in the presence of an acid acceptor, for example an alkali metal alkoxide such as sodium methoxide or potassium tertiary butoxide in the presence of an alkanol. The leaving group Z may itself be formed in situ from the corresponding alkanol (Z=OH) by reaction with a hydrohalogenic acid (e.g. hydrochloric acid or a Lewis acid such as aluminium chloride: see Japanese Patent Kokai No. 131577/77) and the resulting agent of formula (II) reacted directly with imidazole without prior isolation. Alternatively an alkanol (Z=OH) or a derivative thereof (e.g. Z=R—A—O—) may be reacted directly with imidazole (II) by heating in the presence of a dehydrating agent such as phosphoric acid, or a phosphate (see Japanese Patent Publication No. 5 1105 060), sulphuric acid or sulphates (see Japanese Patent Publication No. 5 1105 061).

Among precursor molecules which may be converted to a compound of formula (I) or an acid addition salt thereof, are substituted imidazole derivatives of formula (IV) or addition salts thereof

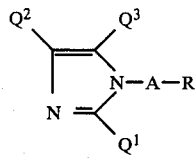

(IV)

wherein A and R are as defined in formula (I), and $Q^1$, $Q^2$ and $Q^3$ are the same or different, at least one being a radical capable of removal by for example reduction or oxidation, the other, or others independently, being a radical having the same function or hydrogen. $Q^1$, $Q^2$ and $Q^3$ may be selected from thio (—SH), alkylthio (-Salkyl wherein alkyl has 1 to 4 carbon atoms) or halo preferably chloro or bromo. The reaction conditions are chosen according to the nature of the removable radicals $Q^1$, $Q^2$ and $Q^3$. Desulphurisation may be performed by oxidative or reductive procedures using for example nitric acid or Raney nickel; and reductive dehalogenation by the use of zinc and acetic acid or Raney nickel or other reagents known in the literature.

Another class of precursors include mono- or dicarboxyimidazoles or derivatives thereof of formula (VI):

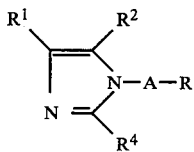

(VI)

wherein A and R are as defined in formula (I), at least one of $R^1$, $R^2$ and $R^4$ is carboxyl or a derivative thereof (for example an ester such as an alkyl ester, an acid halide such as the chloride, or the nitrile) and the other is, or others are independently, hydrogen or carboxyl or a derivative as described. The compounds of formula (VI) may be converted into the imidazoles of formula (I) by any suitable decarboxylation conditions which may simply comprise heating the compounds with or without a catalyst such as copper.

The imidazoles of formula (I) may also be made from a compound of formula (VII):

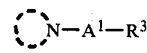

(VII)

wherein ⟨ ⟩N is 1-imidazoline, 1-imidazole or 1-pyrazole, $A^1$ is a straight or branched saturated or unsaturated acyclic hydrocarbon radical, and $R^3$ is a cycloalkyl or cycloalkenyl radical of from 4 to 9 carbon atoms optionally substituted by alkyl as defined in formula (I), provided that at least one of ⟨ ⟩N, $A^1$ and $R^3$ is other than 1-imidazole, a saturated acyclic hydrocarbon and an optionally substituted cycloalkyl group respectively as defined in formula (I). Thus an imidazole (VIII):

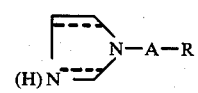

(VIII)

wherein A and R are defined in formula (I) and —indicates an extra bond in either of the positions indicated, may be dehydrogenated to the corresponding imidazole in the presence of a catalyst for example by heating to 250° C. in the presence of palladium, nickel or platinum under pressure, or by heating with a dehydrogenating agent such as selenium or copper oxide. The 1-pyrazole compounds (VII) may be treated with ultra-violet irradiation, optionally under an inert atmosphere (e.g. argon) in for example 1,2-dimethoxyethane at room or elevated temperatures (see for example "Ring Transformations of Heterocycles" edited van der Plas, Academic Press, 1973 at page 261). The unsaturated imidazoles of formula (I) (in formula (VII), $A^1$ and/or $R^3$ are unsaturated) may be reduced to the corresponding saturated compounds e.g. by hydrogenation with a noble metal catalyst, for example platinum or palladium in an alkanol.

The intermediates for use in the above described reactions may also be made by conventional methods known in the art. Thus the 1-pyrazole and 1-imidazoline intermediates (formula (VII)) may be prepared by alkylation of pyrazole and imidazoline in an analogous manner to that described above for preparation of the corresponding imidazoles. The intermediates of formula (III) may be made in known manner preferably by halogenation of the corresponding alcohols (formula (III), Z=OH) where in such compounds R is cycloalkenyl, the alcohol is conveniently prepared by the Prins reaction from the cycloalkene and paraformaldehyde (Bull. Chem. Soc. Japan 46/8, 2512–5, 1973). The substituted imidazole intermediates of formula (IV) may be made in known manner, for example see "Imidazole and its derivatives" Part I, Ed. K. Hoffmann, Interscience Publishers Inc. New York, 1973. For example the 2-thioimidazoles of formula (IV) may be made by cyclisation of an acetal of formula (IX):

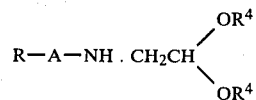

with thiocyanate, wherein $R^4$ is alkyl.

The pharmaceutically acceptable addition salts of the compounds of formula (I) may be prepared by any method known in the art. In particular they may be prepared by treating the parent imidazole with the appropriate acid.

Examples of the addition salts of the compounds of formula (I) include those salts derived from the following acids: oxalic, hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic.

The imidazoles of formula (I) may be used in conjunction with a phosphodiesterase inhibitor, which provides a further, synergistic increase in effect, as it acts against platelet aggregation by a different pathway.

Suitable (cyclic AMP) phosphodiesterase inhibitors for use in potentiating the anti-aggregatory effects of the active compounds include as such or as pharmaceutically acceptable salts:

(a) Xanthine derivatives such as:
Theophylline(3,7-dihydro-1,3-dimethyl-1H-purine-2,6-dione), and salts thereof.
3-Isobutyl-1-methyl-xanthine;
Caffeine(3,7-dihydro-1,3,7-trimethyl-1H-purine-2,6-dione) and salts thereof; and
Aminophylline (adduct of Theophylline and 1,2-ethanediamine (2:1)).

(b) Isoquinoline derivatives, for example:
Papaverine(1-[(3,4-dimethoxyphenyl)methyl]-6,7-dimethoxyisoquinoline) and salts thereof; and
6,7-diethoxy-1-(4,5-diethoxybenzyl)isoquinoline or its salts e.g. its hydrochloride;

(c) Derivatives of pyrimido(5,4-d)-pyrimidine, for example:
Dipyridamole(2,2',2'',2'''-(4,8-dipiperidino-pyrimido[5,4-d]pyrimidin-2,6-diyldinitrilo)-tetraethanol) and its salts;
2,2',2'',2'''-[[4-(1-piperidinyl)pyrimido[5,4-d] pyrimidin-2,6-diyl]dinitrilo]tetrakisethanol and its salts; and
2,4,6-tri-4-morpholinylpyrimido[5,4-d]pyrimidine and its salts.

(d) Derivatives of thieno[3,2-d]pyrimidine, for example:
N-[4-(4-morpholinyl)thieno[3,2-d]pyrimidin-2-yl]-1,2-ethanediamine.

Derivatives of pyrazolo[3',4':2,3]pyrido-[4,5-b][1,5]benzodiazepin-6-(3H)-one, for example:
3-Ethyl-7,12-dihydro-7,12-dimethylpyrazolo-[4',3':5,6]pyrido[4,3-b]-[1,5]benzodiazepin-6-(3H)-one;
3-Ethyl-7,12-dihydro-9-methoxy-7,12-dimethyl-pyrazolo[3',4':2,3]pyrido[4,5-b][1,5]benzodiazepin-6-(3H)-one; and
10-Chloro-3-ethyl-7,12-dimethyl-7,12-dihydropyrazolo[4',3':5,6]pyrido[4,3-b][1,5]benzodiazepin-6-one.

(f) Derivatives of 1H- or 2H-pyrazolo[3,4-b]pyridine, for example:
4-(butylamino)-1-ethyl-1H-pyrazolo[3,4-b]pyridine-5-carboxylic acid ethyl ester;
4-(Butylamino)-1H-pyrazolo[3,4-b]pyridine-6-carboxylic acid ethyl ester;
4-Chloro-1-ethyl-3-methyl-1H-pyrazolo[3,4-b]pyridine-5-acetonitrile;
1-Ethyl-4-(isopropylidenehydrazino)-3-methyl-1H-pyrazolo[3,4-b]pyridine-5-carboxylic acid ethyl ester or its salts such as its hydrochloride hemihydrate; and
2-Methyl-6-phenyl-4-(1-piperidinyl)-2H-pyrazolo-[3,4-b]pyridine or its salts e.g. its hydrochloride.

(g) Derivatives of 5H-furo-[3,4-e]pyrazolo-[3,4-b]pyridine-5-one, for example:
4-(Butylamino)-1-ethyl-1,7-dihydro-7-hydroxy-5H-furo-[3,4-e]pyrazolo[3,4-b]pyridine-5-one; and (h) Derivatives of 1(2H)-naphthalenone, for example:
2-[Dimethylamino)methyl]-3,4-dihydro-7-methoxy-1(2H)-naphthalenone or its salts e.g. its 1:1 hydrochloride.

The active compounds are particularly useful in the treatment and/or prophylaxis of thrombo-embolic disorders in mammals, including man. It is to be understood that the term "thrombo-embolic disorder" includes those disorders whose etiology is associated with platelet aggregation.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts, cerebro-vascular thrombosis and ischaemic peripheral vascular disease; to treat and prevent post-operative thrombosis; and to promote patency of vascular grafts following surgery.

The active compounds are also useful as an addition to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. It may also be used in laboratory animals, e.g. cats, dogs, rabbits, monkeys and rats, for these purposes in order to develop new methods and techniques for organ and limb transplants.

The active compounds also exhibit some vasodilatory action on blood vessels and therefore have a utility as anti-hypertensives for the treatment of high blood pressure in mammals, including man.

The active compounds may also be used in the prevention, treatment or prophylaxis of angina pectoris, and in the prevention or delay of onset of shock.

The amount of active compound required for therapeutic or prophylactic effect will vary with the route of administration, and the nature of the condition under treatment. In general a suitable dose for a mammal, including man, of active compound will lie in the range of 0.1 to 300 mg per kg of body weight, particularly from 0.5 to 10 mg per kg of body weight, for example 2 mg per kg. A suitable single oral dose for an adult human lies within the range of 50 to 600 mg, for example 150 mg given say three times a day.

While it is possible for an active compound to be administered as the raw chemical it is preferable to present it as a pharmaceutical formulation. The formulations, both for veterinary and for human medical use, of the present invention comprise an active compound as above defined, together with one or more acceptable carriers therefor and optionally other therapeutic ingredients. The carrier(s) must be 'acceptable' in the sense of being compatible with the other ingredients of the formulation and not deleterious to the recipient thereof. Unit doses of a formulation may contain between 60 mg and 1.5 g of an active compound.

The formulations include those suitable for oral, rectal, vaginal or parenteral (including subcutaneous, intramuscular or intravenous) administration. Preferred formulations include tablets, capsules and injectable suspensions or solutions.

The formulations may conveniently be presented in unit dosage form and may be prepared by any of the methods well known in the art of pharmacy. All methods include the step of bringing into association the active compound (in the form of the base or a pharmaceutically acceptable acid addition salt) with the carrier which constitutes one or more accessory ingredients. In general the formulations are prepared by uniformly and intimately bringing into association the active compound with liquid carrier(s) or finely divided solid carrier(s) or both, and then, if necessary, shaping the product into the desired formulation.

It will be appreciated from the foregoing that the present invention provides the following features:

(a) Novel 1-alkylimidazoles of formula (I), and acid addition salts thereof.

(b) Methods of preparing imidazoles of formula (I) and acid addition salts thereof.

(c) Pharmaceutical formulations containing an imidazole of formula (I) or an acid addition salt thereof and a pharmaceutically acceptable carrier.

(d) Method of preparing the pharmaceutical formulations containing the imidazoles of formula (I) or an acid addition salt thereof.

(e) A method for the treatment or prophylaxis of a thrombo-embolic disorder in a mammal or mammalian tissue, including man or human tissue, comprising administering an active compound.

(f) A method of prevention, treatment or prophylaxis of angina pectoris in a mammal, including man, which comprises administering to the mammal an effective amount of an imidazole of formula (I) or a pharmaceutically acceptable acid addition salt thereof.

(g) A method of preventing or delaying the onset of shock in a mammal, including man, which comprises administering to the mammal an effective amount of an imidazole of formula (I) or a pharmaceutically acceptable salt thereof.

EXAMPLE 1

1-Cyclooctylmethylimidazole

Imidazole (2.0 g, 0.03 mol) was added to a solution of sodium (0.7 g, 0.03 mol) in dry ethanol (50 ml). The mixture was stirred and heated to boiling when bromomethylcyclooctane (5.5 g, 0.027 mol) was added dropwise. Following the addition, the reaction mixture was stirred and boiled for 15 h.

After cooling, the reaction mixture was filtered, and the filtrate concentrated under reduced pressure. The residue was dissolved in 2 M-hydrochloric acid (100 ml) and the solution washed with ether (25 ml). The aqueous layer was basified with 10 M-sodium hydroxide solution and then extracted with chloroform (3×50 ml). The chloroform extracts were combined and dried ($MgSO_4$). Evaporation of the chloroform gave an oil which was purified using a silica gel column and elution with ethyl acetate/methanol (9:1). The product was further purified by distillation, b.p. 120°–122°/0.2 mmHg.

EXAMPLE 2

Preparation of 1-cyclopentylmethylimidazole

Imidazole (6.8 g, 0.1 mol) was added to a solution of sodium (2.3 g, 0.1 mol) in dry ethanol (100 ml). This solution was stirred and heated to reflux when bromomethylcyclopentane (16.3 g, 0.1 mol) was added dropwise. Following the addition, the mixture was stirred and heated under reflux for 16 h.

After cooling, the reaction mixture was filtered and the filtrate concentrated under reduced pressure. The residue was dissolved in 2 M-hydrochloric acid (150 ml) and the solution washed with ether. The aqueous solution was basified with 10 M-sodium hydroxide solution, and the product extracted with chloroform (3×50 ml). The extracts were combined, dried ($MgSO_4$), and the solution concentrated to afford a yellow oil.

The oil was purified using a silica gel column and elution with ethyl acetate/methanol (9:1). The product fractions were combined and concentrated under reduced pressure to afford 1-cyclopentylmethylimidazole (1.9 g), which was further purified by distillation, b.p. 68°–69°/0.125 mmHg.

EXAMPLE 3

Preparation of 1-(3-cyclopentylpropyl)imidazole

Imidazole (1.0 g, 0.0147 mol) was added to a solution of sodium (0.34 g, 0.0148 mol) in dry ethanol (30 ml). This solution was stirred and heated to boiling when 3-bromopropylcyclopentane (2.94 g, 0.0154 mol) was added dropwise. Following the addition, the reaction mixture was stirred and boiled for 20 h.

After cooling, the mixture was filtered and the filtrate concentrated under reduced pressure. The residue was dissolved in 2 M-hydrochloric acid (50 ml) and the solution washed with ether (25 ml). The acid solution was then basified with 10 M-sodium hydroxide solution, and the product extracted with chloroform (3×25 ml). The combined extracts were dried ($MgSO_4$) and concentrated under reduced pressure to afford a yellow oil (2.1 g).

The oil was purified by column chromatography (silica gel) using ethyl acetate/methanol (9:1) as eluent. The product fractions were combined and concentrated to afford 1-(3-cyclopentylpropyl)imidazole which was further purified by distillation, b.p. 89°–90°/0.1 mmHg.

EXAMPLE 4

Preparation of 1-(cycloheptylmethyl)imidazole

Bromomethylcycloheptane (5.3 g, 0.0278 mol) was added dropwise to a stirred solution of potassium t-butoxide (3.1 g, 0.0277 mol) and imidazole (1.9 g, 0.0279 mol) in dry n-butanol (50 ml) maintained at 100° and under dry nitrogen. After the addition (~20 mins) the temperature of the reaction mixture was raised to boiling. The reaction mixture was then stirred and boiled for 7 h and then cooled.

The mixture was filtered, and the n-butanol was removed under reduced pressure to give a pale yellow oil. The oil was dissolved in 2 M-hydrochloric acid (100 ml) and the acid solution was washed with ether (100 ml) and then basified with 10 M-sodium hydroxide solution and the resulting suspension was extracted with chloroform (3×50 ml). The chloroform extracts were combined, dried ($MgSO_4$), and concentrated under reduced pressure to give a pale yellow oil.

The oil was purified using a silica gel column and elution with ethyl acetate/methanol (9:1). Concentration of the fractions containing 1-(cycloheptylmethyl)imidazole gave a pale yellow oil which was further purified by distillation, b.p. 92°–94°/0.1 mmHg.

EXAMPLE 5

Preparation of 1-(2-cyclooctenylmethyl)imidazole (a) Preparation of 2-cyclooctene-1-methanol using the Prins reaction (Uchida et al., *Bull. Chem. Soc., Japan,* 1973 46, 2512)

Cyclooctene (69.0 g, 0.63 mol) was added dropwise, to a stirred suspension of paraformaldehyde (24.0 g) in 98% formic acid (100 ml). After the addition, the reaction mixture was stirred and heated under reflux for 2 h. Water (100 ml) was then added, and the aqueous solution was extracted with ether (50 ml). The ether solution was washed with saturated sodium bicarbonate solution (5×50 ml), with water (2×50 ml), and then dried ($MgSO_4$). Concentration under reduced pressure afforded a brown oil which was purified by distillation, the fraction b.p. 80°–110°/24 mmHg being retained.

A portion of the aforesaid oil (10 g) was treated with Claisen's alkali [potassium hydroxide (10 g), methanol (31.2 ml) and water (8 ml)], and the reaction mixture was then boiled for 2 h.

After cooling, the mixture was poured onto iced-water (50 ml) and extracted with ether (3×50 ml). The ether extracts were combined and dried ($MgSO_4$). Concentration of the solution under reduced pressure afforded an oil which was distilled, to afford 2-cyclooctene-1-methanol, b.p. 128°–130°/23 mmHg.

(b) Preparation of 2-cyclooctene-1-bromomethane

A solution of phosphorus tribromide (1.02 ml, 0.0105 mol) in petroleum ether (b.p. 40°–60°, 5 ml) was added dropwise to a stirred solution of 2-cyclooctene-1-methanol (2.8 g, 0.02 mol) and dry pyridine (0.104 g, 0.0013 mol) in petroleum ether (b.p. 40°–60°; 15 ml) at −10°. After the addition, the reaction mixture was set aside at ambient temperature for 48 h.

The reaction mixture was treated with water (50 ml) and the organic layer separated. The aqueous solution was extracted with petroleum ether (b.p. 40°–60°, 3×25 ml) and the organic layer and petroleum ether extracts combined, washed with 2 M-sodium hydroxide solution (25 ml), and with water (25 ml), and then dried ($MgSO_4$). Concentration of the solution under reduced pressure gave an oil (2.3 g) which was distilled, b.p. 48°–50°/0.25 mmHg.

(c) Preparation of 1-(2-cyclooctenylmethyl)imidazole

2-Cyclooctene-1-bromomethane (0.7 g, 0.0034 mol) was added dropwise to a boiling solution of imidazole (0.24 g, 0.0035 mol) and potassium t-butoxide (0.39 g, 0.0035 mol) in dry n-butanol, under dry nitrogen. After the addition, the reaction mixture was stirred and heated under reflux for 1 h. The pure product was obtained as described in Example 4, b.p. 108°–110°/0.02 mmHg.

EXAMPLE 6

Preparation of 1-(4-methylcyclohexylmethyl)imidazole

1-Bromomethyl-4-methylcyclohexane (3.1 g, 0.0162 mol) was added dropwise to a stirred, boiling solution of imidazole (1.12 g, 0.0165 mol) and potassium t-butoxide (1.85 g, 0.0165 mol) in dry n-butanol, under dry nitrogen. After the addition, the reaction mixture was stirred and heated under reflux for 10 h.

After cooling, the reaction mixture was filtered, and then concentrated under reduced pressure. The residue was dissolved in 2 M-hydrochloric acid (100 ml) and the solution was washed with ether (50 ml). The acid solution was basified with 10 M-sodium hydroxide solution and extracted with chloroform (3×50 ml). The combined chloroform extracts were dried ($MgSO_4$) and concentrated under reduced pressure. The oily residue was purified using a silica gel column and elution with ethyl acetate/methanol (9:1). The fractions containing 1-(4-methylcyclohexylmethyl)imidazole were combined, concentrated, and the resulting oil distilled, b.p. 80°/0.125 mmHg.

EXAMPLE 7

Preparation of 1-[2-(Cyclohex-3-enyl)ethyl]imidazole

1-Chloro-2-(cyclohex-3-enyl)ethane (38.0 g, 0.265 mol) was added dropwise to a stirred, boiling solution of potassium tert-butoxide (30.0 g, 0.27 mol) and imidazole (18.0 g, 0.265 mol) in dry butan-1-ol. Following the addition, the reaction mixture was stirred and heated under reflux for 4 h.

After cooling, the reaction mixture was filtered, and filtrate was evaporated under reduced pressure to afford a brown oil. The oil was dissolved in hydrochloric acid (100 ml, 2 M), and the acid solution was washed with ether (3×100 ml). The acid solution was then basified with sodium hydroxide (10 M), and the basic solution was extracted with chloroform (3×100 ml). The chloroform extracts were combined and dried ($MgSO_4$). Evaporation of the chloroform afforded a brown oil which was purified using a silica gel column and by elution with chloroform/methanol (9:1). The product fractions were pooled and concentrated to give an oil which was distilled, to afford 1-[2-cyclohex-3-enyl)ethyl]imidazole, b.p. 83°–84°/0.02 mm Hg.

EXAMPLE 8

Biological Results

Horse platelets were prepared from whole horse blood by differential centrifugation. Approximately $10^6$ platelets were homogenised in 1 ml 100 mM Tris buffer pH 7.4. Various concentrations of active compound were added and the reaction sets incubated for 5 minutes at ambient temperature. To each acid tube was added 20 nM of arachidonic acid containing $10^6$ DPM of labelled arachidonic acid and the tubes incubated for 3 minutes at 37° C. in a shaking water bath. After incubation the radioactive products were extracted from the acidified aqueous phase with ethyl acetate and after concentration resolved by thin layer chromatography on silica gel with chloroform/methanol/acetic acid/water (90:8:1:0.8) as a developing solvent. The amount of thromboxane produced was measured by scraping the radioactive zone corresponding to thromboxane $B_2$ and estimating the radioactivity in a liquid scintillation counter.

The concentration of active compound to reduce the enzyme activity by 50% ($ED_{50}$) was established. The results are shown in Table A.

The selectivity of the active compounds was measured in a similar manner to that described above and the amount of PGE, PGF and PGD produced was determined. The greater the selectivity, the more of the prostaglandins are produced indicating lower inhibition of cyclo-oxygenase.

The ED$_{50}$ and Selectivity results are shown in Table A in which 0 indicates no selectivity; + low selectivity; ++ medium selectivity; and +++ high selectivity.

TABLE A

| Compound (Reference Compound) | ED$_{50}$ μg/ml | Selectivity |
|---|---|---|
| (Imidazole) | 500 | 0 to + |
| (1-Methylimidazole) | 200 | ++ |
| 1-Cyclopentylmethylimidazole | ~5 | +++ |
| 1-(2-Cyclohexylethyl)imidazole | 4 | +++ |
| 1-Cyclooctylmethylimidazole | 4 | +++ |
| 1-Cyclohex-3-enylmethylimidazole | ~5 | +++ |
| 1-Cyclobutylmethylimidazole | 50 | +++ |
| 1-Cycloheptylmethylimidazole | 4.7 | ++++ |
| 1-(4-Methylcyclohexylmethyl)-imidazole | 6.6 | +++ |
| 3-Cyclopentylpropylimidazole | 2.4 | (+) |
| 1-(2-Cyclooctenylmethyl)imidazole | 3.4 | +++ |

EXAMPLE 9

Tablet formulation

| 1-Cyclooctylmethylimidazole (as a salt) | 150 mg |
|---|---|
| Starch | 25 mg |
| Polyvinylpyrrolidone | 2 mg |
| Magnesium stearate | 3 mg |

The imidazole salt is ground to a fine powder blended with the starch and then the mixture granulated with an aqueous solution of the polyvinylpyrrolidone. The granules are sieved 1000μ, dried, sieved again and the magnesium stearate added. The mixture is then compressed into tablets.

In the same manner, tablets of 1-cyclohex-3-enylmethylimidazole, 1-(2-cyclohexylethyl)imidazole or 1-cycloheptylmethylimidazole are prepared.

EXAMPLE 10

Tablet formulation

Tablets (150 mg) of the imidazoles described in the preceding Example are prepared in the same manner from the following ingredients:

| The Imidazole Compound (as a salt) | 150 mg |
|---|---|
| Lactose | 100 mg |
| Starch | 30 mg |
| Polyvinylpyrrolidone | 2 mg |
| Magnesium stearate | 3 mg |

In the preparation, the lactose is blended with the starch.

EXAMPLE 11

Tablet formulation

Tablets (100 mg) of the imidazoles of Example 9 are prepared in the same manner from the following ingredients:

| The Imidazole Compound (as a salt) | 100 mg |
|---|---|
| Sodium starch glycolate | 10 mg |
| Polyvinylpyrrolidone | 2 mg |
| Magnesium stearate | 3 mg |

EXAMPLE 12

Tablet formulation

Tablets (150 mg) of the imidazoles of Example 9 are prepared in the same manner from the following ingredients, except that the starch, pregelled starch and imidazole compound are all blended together prior to granulation:

| The Imidazole Compound (as a salt) | 150 mg |
|---|---|
| Starch | 25 mg |
| Pregelled starch | 5 mg |
| Magnesium stearate | 3 mg |

Example 13

Injectable formulation

| Imidazole compound of formula (I) | 15.0 g |
|---|---|
| Lactic Acid B.P. | q.s. to pH 3.0 |
| Water for Injections | to 100.0 ml |

Suspend the compound in ¾ of the available quantity of water. Add sufficient Lactic Acid to dissolve the compound and to reduce the pH to 3.0. Dilute to volume with Water for Injections.

Sterilise the solution by passage through a membrane filter, pore size 0.22 μm.

Distribute the solution using aseptic precautions into sterilised ampoules, 1 ml per ampoule. Seal by fusion of the glass.

Each 1 ml ampoule supplies 150 mg of the imidazole compound: 1-cyclooctylmethylimidazolefumarate.

EXAMPLE 14

Injectable formulation

| Imidazole compound of formula (I) | 15.0 g |
|---|---|
| Citric Acid B.P. | q.s. to pH 3.0 |
| Chlorocresol | 0.1 g |
| Water for Injections to | 100.0 ml |

Suspend the compound in ½ the final volume of Water for Injections. Add sufficient Citric Acid as a 10% solution in Water for Injections to dissolve the compound and reduce the pH to 3.0. Dilute to volume with Water for Injections.

Sterilise the solution by passage through a membrane filter, pore size 0.22 μm.

Distribute the solution with aseptic precautions into sterilised vials, 25 ml per vial. Stopper with sterile rubber closures and seal with an aluminium cap.

Each 1 ml of solution provides 150 mg of the compound: 1-cyclooctylmethylimidazole fumarate.

EXAMPLE 15

Injectable formulation

In the manner described in the preceding two Examples, injectable formulations of 1(2-cyclohexylethyl)imidazole, 1-cycloheptylmethylimidazole and 1-cyclohex-3-enylmethylimidazole salts were prepared.

EXAMPLE 16

By the method described in Example 1 above the following compounds were prepared:

(a) 1-(cyclooctylvinyl)imidazole
(b) 1-(1-cyclooctylethyl)imidazole
(c) 1-(2-cyclooctylethyl)imidazole
(d) 1-(3-cyclooctylpropyl)imidazole
(e) 1-(3-methylcyclohept-2-enylmethyl)imidazole
(f) 1-(3-methylcycloheptylmethyl)imidazole
(g) 1-(cyclohex-3-enylmethyl)imidazole m.p. 36°–37° C.
(h) 1-(2-cyclohexylethyl)imidazole b.p. 95°–96°/0.2 mm
(i) 1-(cyclobutylmethyl)imidazole b.p. 148°–150°/25 mm.

EXAMPLE 17

Salts of 1-cyclooctylmethylimidazole

A. Hydrogen Fumarate

A solution of fumaric acid (0.22 g) in hot ethanol (10 ml) was added to a solution of 1-cyclooctylmethyl imidazole (0.38 g) in ethanol (4 ml). After boiling for 10 minutes the solution was evaporated to afford a white solid. Recrystallisation from ethyl acetate afforded 1-cyclooctylmethylimidazole hydrogen fumarate (0.42 g) as white needles, m.p. 147° to 148° C.

B. Hydrogen Succinate

A solution of succinic acid (0.23 g) in ethanol (~5 ml) was added to a solution of 1-cyclooctylmethylimidazole (0.38 g) in ethanol (5 ml). Evaporation of the solution afforded a white solid. Recrystallisation of the solid from ethyl acetate afforded 1-cyclooctylmethylimidazole hydrogen succinate (0.27 g) as colourless plates, m.p. 86° to 87° C.

C. Oxalate

A solution of oxalic acid (0.17 g) and 1-cyclooctylmethylimidazole (0.38 g) in ethanol (20 ml) was boiled for 0.25 hour, when evaporation of the solution afforded a white solid. Recrystallisation of the solid from ethyl acetate/ethanol/petroleum ether (b.p. 40°–60°) afforded 1-cyclooctylmethylimidazole oxalate as white needles, m.p. 141°–142° C.

D. Hydrochloride

1-Cyclooctylmethylimidazole (~0.3 g) was dissolved in dry ether (30 ml), when a stream of dry hydrogen chloride was passed through the solution at −20° C. The resulting white precipitate was filtered off under dry nitrogen and recrystallised from ethyl acetate/petroleum ether (b.p. 40°–60° C.) to afford 1-cyclooctylmethylimidazole hydrochloride as a white solid, m.p. 20°–22° C.

I claim:

1. A method of treating a mammal in a state of shock, which comprises administering to the mammal an effective amount of a compound of the formula

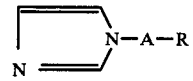

in which A is selected from the group consisting of straight or branched, saturated or unsaturated acyclic hydrocarbon radicals of from 1 to 3 carbon atoms and R is selected from the group consisting of cycloalkyl or cycloalkenyl groups of from 4 to 9 carbon atoms optionally substituted by one, two, three or more alkyl groups each containing from 1 to 4 carbon atoms, with the proviso that when A is a methylene radical, R is not unsubstituted cyclohexyl, the alkylimidazole being the free base or a pharmaceutically acceptable salt thereof.

2. The method of claim 1 wherein said compound is administered in the amount of from 0.1 to 300 mg per kg body weight of said mammal.

3. The method of claim 1 wherein said compound is administered in the amount of from 0.5 to 10 mg per kg body weight of said mammal.

4. The method of claim 1 wherein said compound is administered in the amount of 2 mg per kg body weight of said mammal.

5. The method of claim 1 wherein said compound is administered orally.

6. The method of claim 1 wherein said compound is administered parenterally.

7. The method of claim 1 wherein said compound is administered in the form of a tablet.

8. The method of claim 1 wherein said compound is administered in the form of a capsule.

9. The method of claim 1 wherein said compound is administered in the form of an injectable suspension or solution.

10. The method of claim 1 wherein the mammal is an adult human and said compound is administered orally in the amount of from 50 to 600 mg.

11. The method of claim 10 wherein said compound is administered in the amount of 150 mg three times a day.

* * * * *